US012788589B2

(12) United States Patent
Barfield

(10) Patent No.: US 12,788,589 B2
(45) Date of Patent: Nov. 10, 2026

(54) ACETABULAR CUP REMOVER ASSEMBLY

(71) Applicant: MicroPort Orthopedics Holdings Inc., Arlington, TN (US)

(72) Inventor: Charles Barfield, Memphis, TN (US)

( * ) Notice: Subject to any disclaimer, the term of this patent is extended or adjusted under 35 U.S.C. 154(b) by 568 days.

(21) Appl. No.: 18/153,127

(22) Filed: Jan. 11, 2023

(65) Prior Publication Data

US 2023/0248539 A1 Aug. 10, 2023

Related U.S. Application Data

(60) Provisional application No. 63/267,618, filed on Feb. 7, 2022.

(51) Int. Cl.
*A61B 17/16* (2006.01)
*A61B 17/17* (2006.01)
*A61F 2/46* (2006.01)

(52) U.S. Cl.
CPC ........ *A61F 2/4609* (2013.01); *A61B 17/1746* (2013.01); *A61F 2002/4619* (2013.01)

(58) Field of Classification Search
CPC ........... A61F 2/4609; A61F 2002/4619; A61B 17/1746
See application file for complete search history.

(56) References Cited

U.S. PATENT DOCUMENTS 4,941,466 A * 7/1990 Romano ............ A61B 17/1642 408/127
5,112,338 A 5/1992 Anspach, III
5,290,315 A 3/1994 DeClarlo, Jr.
6,013,082 A 1/2000 Hiernard et al.
6,132,469 A 10/2000 Schroeder
6,565,575 B2 5/2003 Lewis
6,905,502 B2 6/2005 Penenberg
6,997,928 B1 2/2006 Penenberg
7,651,501 B2 1/2010 Penenberg (Continued)

FOREIGN PATENT DOCUMENTS

EP 0149642 6/1988
KR 101402893 6/2014

(Continued)

OTHER PUBLICATIONS

Innomed, Instrument Update, brochure, Jan. 2012.

(Continued)

*Primary Examiner* — Tracy L Kamikawa

(57) ABSTRACT

A cup remover instrument assembly for removing an acetabular cup in a revision hip procedure comprising: a positioning member supporting a cutting assembly having a cutting blade and a detachable drive member for selectively rotating the cutting assembly to cut around a cup to detach the cup from a patient's natural acetabulum. In embodiments, the positioning member is sized and configured to operate in a main incision, while the drive member is sized and configured to operate in a portal incision. In embodiments, the cutting blade is detachable for use in selecting blades for cup sizes. In embodiments, the cutting blade is selectively extendable from the cutting assembly. In other embodiments, the cutting blade is hemispherical and is rotated by a power driver.

9 Claims, 12 Drawing Sheets

(56) References Cited

U.S. PATENT DOCUMENTS

| | | | | |
|---|---|---|---|---|
| 7,763,031 | B2 * | 7/2010 | Tulkis ................ | A61B 17/1666 606/81 |
| 7,833,229 | B2 | 11/2010 | Penenberg | |
| 8,439,928 | B2 | 5/2013 | Penenberg | |
| 8,834,480 | B2 | 9/2014 | Hudak, Jr. et al. | |
| 9,180,023 | B2 | 11/2015 | Penenberg | |
| 9,539,113 | B2 | 1/2017 | Penenberg | |
| 9,724,209 | B2 * | 8/2017 | Kim ................... | A61B 17/1666 |
| 9,763,676 | B2 | 9/2017 | Motherway et al. | |
| 10,342,553 | B2 | 7/2019 | Gilhooley | |
| 10,441,436 | B2 | 10/2019 | Termanini et al. | |
| 10,463,507 | B2 * | 11/2019 | Nic .................... | A61B 17/1666 |
| 11,147,689 | B2 | 10/2021 | Nic | |
| 11,484,417 | B2 | 11/2022 | Joo | |
| 2002/0116007 | A1 | 8/2002 | Lewis | |
| 2004/0153080 | A1 | 8/2004 | Dong et al. | |
| 2006/0200165 | A1 | 9/2006 | Tulkis | |
| 2007/0021766 | A1 | 1/2007 | Belagali et al. | |
| 2008/0009874 | A1 | 1/2008 | Meridew et al. | |
| 2008/0195111 | A1 | 8/2008 | Anderson | |
| 2012/0184964 | A1 | 7/2012 | Hudak, Jr. et al. | |
| 2016/0100957 | A1 | 4/2016 | Lewis | |
| 2020/0121474 | A1 | 4/2020 | Pendelton et al. | |
| 2021/0154025 | A1 | 5/2021 | Slater | |

FOREIGN PATENT DOCUMENTS

| | | | |
|---|---|---|---|
| WO | 2012010366 | A1 | 1/2012 |
| WO | 2013046172 | A1 | 4/2013 |
| WO | 2015155657 | | 10/2015 |
| WO | 2017180602 | A1 | 10/2017 |

OTHER PUBLICATIONS

Zimmer, Explant Acetabular Cup Removal System Surgical Technique. Supporting documentation, 2011.

Arillo J. Fernandez, Communication-European Search Report, Letter, Dec. 14, 2023, 7 pages, European Patent Office, Munich, Germany.

Fernandez Arillo J, European Search Report; Communication Report; Jun. 14, 2023; 1-7; European Patent Office; Munich, Germany.

* cited by examiner

ACETABULAR CUP REMOVER ASSEMBLY

REFERENCE TO RELATED APPLICATION

This application claims the benefit of U.S. Provisional Application No. 63/267,618 filed Feb. 7, 2022. The disclosure of this related application is hereby incorporated into this disclosure in its entirety.

BACKGROUND OF THE INVENTION

1. Technical Field

The present disclosure relates to instruments and methods for orthopedic surgery, and more particularly to instruments and methods for the removal of acetabular hip cup implants in total hip arthroplasties.

2. Related Art

In a total hip arthroplasty ("THA"), deteriorated cartilage in the acetabulum is replaced with an artificial hip cup. The artificial hip cup interacts with a ball head of an artificial hip stem to provide an artificial hip joint. In some hip implant designs, the cup consists of a unibody cup that is secured in the acetabulum, such as by bone ingrowth, bone cement, or screws. In other hip implant designs, the cup comprises an outer shell that is secured in the acetabulum in the foregoing manner and a separate cup liner that is inserted in the shell between the outer shell and the ball head of the artificial hip stem.

The initial or "primary" hip implant typically lasts in a patient for about ten to twenty years. When the primary hip implant wears out, it is often useful to "revise" the primary hip implant by replacing it with new components. Revision typically includes removal and replacement of the primary acetabular cup. Additionally, when a revision cup wears out, it is typically desirable to remove and replace it.

Examples of prior cup removers that use a cutting blade to loosen the hip cup from the acetabulum include the cup removers disclosed in PCT App. No. WO2015/155657 (to Giardiello, et. al) and U.S. Pat. No. 6,565,575 (to Lewis). However, these designs are intended for use in conventional THAs. A THA is typically performed through a relatively large incision (e.g., between 8 to 12 inches) to provide sufficient access to the joint. The large incision also permits the introduction and manipulation of instruments within the joint. Large incisions may increase operating time and cause patients to lose substantial amounts of blood, inflict significant trauma to surrounding tissues (e.g., the nerves and muscles), increase the risk of infection, and require longer recovery periods.

Furthermore, the Giardiello and Lewis devices have modular cutting blades of different lengths and curvatures. A short thick blade may be used to start an opening between the hip cup and the acetabulum, while a longer increasingly curved blade may be used to expand the opening and remove the hip cup. These devices require that the cup remover be partially disassembled prior to replacing the modular cutting blades. This practice increases procedure duration and therefore necessarily increases the surgery's ancillary risks, including the infection risk and the possibility of complications arising from increased time under anesthesia.

In recent years, efforts have been made to develop "minimally invasive" procedures that reduce the incision length required for THA, with the aim of reducing blood loss, trauma, risk of infection, and recovery time. See U.S. Pat. No. 6,905,502 (to Brad Penenberg, M.D.) and its family members (e.g., U.S. Pat. Nos. 6,997,928; 7,833,229; and 6,997,928), each of which is incorporated herein by reference in its entirety. These patents describe the earliest efforts to use a small portal incision in conjunction with a larger main incision in order to prepare the acetabulum for receipt of a hip implant using a posterior approach. Refinements of these instruments and methods are described in U.S. Pat. No. 7,651,501 (to Brad Penenberg, M.D.) and its progeny (e.g., U.S. Pat. Nos. 8,439,928; 9,180,023; and 9,539,113), each of which is incorporated herein by reference in its entirety. In these methods, a specially configured guide is placed into the main incision. A portion of the guide is placed in the acetabulum to provide a reference point. An outrigger structure extends from the guide outside of the main incision. An outer portion of the outrigger includes a guide for guiding instruments such as trocars and cannulas into alignment with the acetabulum. The guide is used to form a small posterior portal incision in alignment with the acetabulum, as well as to hold a cannula and to guide instruments during preparation of the acetabulum. By using a small posterior portal incision in conjunction with a main incision, the length of the main incision can be reduced to about the size of the acetabular cup, such as 2 to 3 inches.

However, when it comes to revision procedures, cup removal instruments have remained wedded to the single incision concept. There is a need for cup removers that can be used in minimally invasive two-incision techniques. Thus, there is a need for the techniques described herein below, which enable a reduced incision, good visualization, and other benefits that have not been obtained in conventional revision procedures.

SUMMARY OF THE INVENTION

The problems associated with lengthy procedure duration and a large incision in a revision hip arthroplasty, including but not necessarily limited to an increased risk of patient infection, significant blood loss, trauma to the surrounding tissue, increased healing times, and complications arising from prolonged time under anesthesia can be mitigated by the assemblies or methods, or a combination of assemblies and methods in accordance with this disclosure. One such exemplary medical device assembly can comprise: an orientation bearing having an inner surface defining a hole, a positioning member engaged to the orientation bearing, the positioning member having a longitudinal body extending between a leading end and a trailing end, a cutting assembly having a mating portion configured to be rotatably disposed within the hole of the orientation bearing, wherein the cutting assembly comprises a cutting blade, and, a drive member having a drive member body extending between a drive member leading end and a drive member trailing end, wherein the drive member trailing end is configured to engage the cutting assembly to rotatably drive the cutting assembly.

It is contemplated that certain exemplary embodiments in accordance with the present disclosure may provide an acetabular cup remover instrument assembly for use in hip arthroplasty revision procedures.

It is contemplated that certain exemplary embodiments in accordance with the present disclosure may provide a cup remover assembly configured for use in minimally invasive hip procedures carried out through a primary and a portal incision.

It is further contemplated that certain exemplary embodiments in accordance with the present disclosure may provide an acetabular cup remover assembly configured for use with a cannula in hip arthroplasty procedures.

Methods of using the instrument assembly and presenting the parts of the exemplary assemblies in kits are also described.

The foregoing and other features, aspects and advantages of the invention will become more apparent from the following detailed description of the invention when considered in conjunction with the accompanying drawings.

DETAILED DESCRIPTION OF THE PREFERRED EMBODIMENTS

Figure 1:
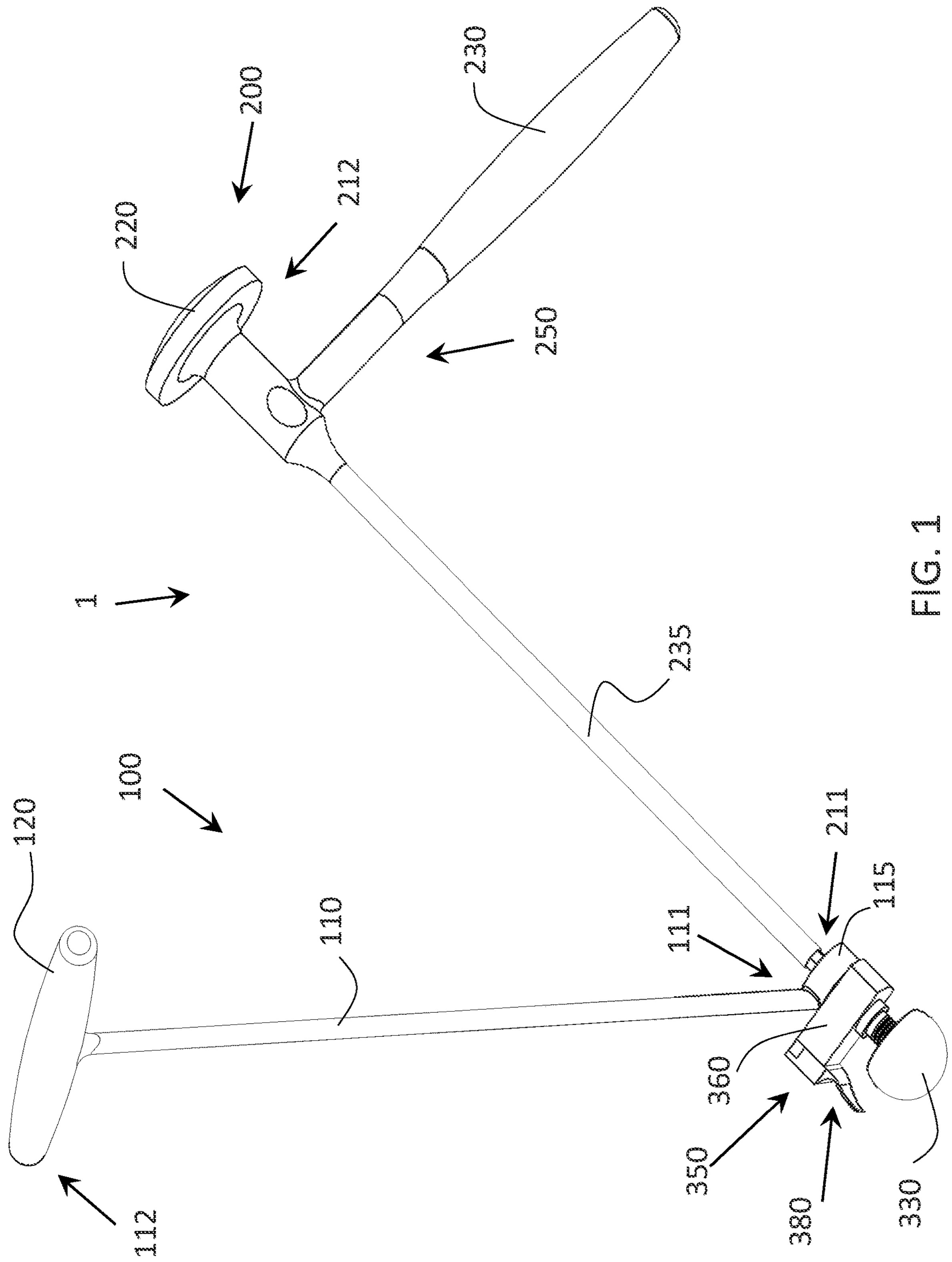
FIG. 1 is a front-side perspective view of one exemplary embodiment of an acetabular cup remover assembly in the assembled configuration featuring a single fixed cutting blade.

In the following detailed description of the preferred embodiments, reference is made to the accompanying drawings which form a part hereof, and in which are shown by way of illustration, specific embodiments in which the invention may be practiced. It is to be understood that other embodiments may be utilized and structural changes may be made without departing from the scope of the present invention.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Similar reference characters indicate corresponding parts throughout the several views unless otherwise stated. Although the drawings represent embodiments of various features and components according to the present disclosure, the drawings are not necessarily to scale and certain features may be exaggerated to better illustrate embodiments of the present disclosure, and such exemplifications are not to be construed as limiting the scope of the present disclosure.

Except as otherwise expressly stated herein, the following rules of interpretation apply to this specification: (a) all words used herein shall be construed to be of such gender or number (singular or plural) as such circumstances require; (b) the singular terms "a," "an," and "the," as used in the specification and the appended claims include plural references unless the context clearly dictates otherwise; (c) the antecedent term "about" applied to a recited range or value denotes an approximation with the deviation in the range or values known or expected in the art from the measurements; (d) the words, "herein," "hereby," "hereto," "hereinbefore," and "hereinafter," and words of similar import, refer to this specification in its entirety and not to any particular paragraph, claim, or other subdivision, unless otherwise specified; (e) descriptive headings are for convenience only and shall not control or affect the meaning of construction of part of the specification; and (f) "or" and "any" are not exclusive and "include" and "including" are not limiting. Further, the terms, "comprising," "having," "including," and "containing" are to be construed as open-ended terms (i.e., meaning "including but not limited to").

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether explicitly described.

To the extent necessary to provide descriptive support, the subject matter and/or text of the appended claims are incorporated herein by reference in their entirety.

Recitation of ranges of values herein are merely intended to serve as a shorthand method of referring individually to each separate value falling within the range of any subranges there between, unless otherwise clearly indicated herein. Each separate value within a recited range is incorporated into the specification or claims as if each separate value were individually recited herein. Where a specific range of values is provided, it is understood that each intervening value, to the tenth or less of the unit of the lower limit between the upper and lower limit of that range and any other stated or intervening value in that stated range of sub range thereof, is included herein unless the context clearly dictates otherwise. All subranges are also included. The upper and lower limits of these smaller ranges are also included therein, subject to any specifically and expressly excluded limit in the stated range.

It should be noted that some of the terms used herein are relative terms. For example, the terms, "upper" and "lower," "above" and "below" are relative to each other in location, i.e., an upper component is located at a higher elevation than a lower component in the indicated or depicted orientation, but these terms can change if the orientation is flipped.

The terms, "horizontal" and "vertical" are used to indicate direction relative to an absolute reference, i.e., ground level. However, these terms should not be construed to require structure to be absolutely parallel or absolutely perpendicular to each other. For example, a first vertical structure and a second vertical structure are not necessarily parallel to each other.

As indicated in FIGS. 1-7, exemplary embodiments of the detachable acetabular cup remover instrument assembly 1 are configured for use in removing a primary acetabular cup or combination of cup and shell 400 (FIG. 2A) (collectively, "primary cup") in a revision hip procedure. Although the instrument 1 is described herein for removal of primary cups, it can be used to remove revision cups when revision cups are present.

The exemplary cup remover instrument assemblies 1 described herein have an assembled configuration (see e.g., FIG. 2A), a disassembled configuration (see FIG. 2B), and partially assembled configurations.

Figure 2A:
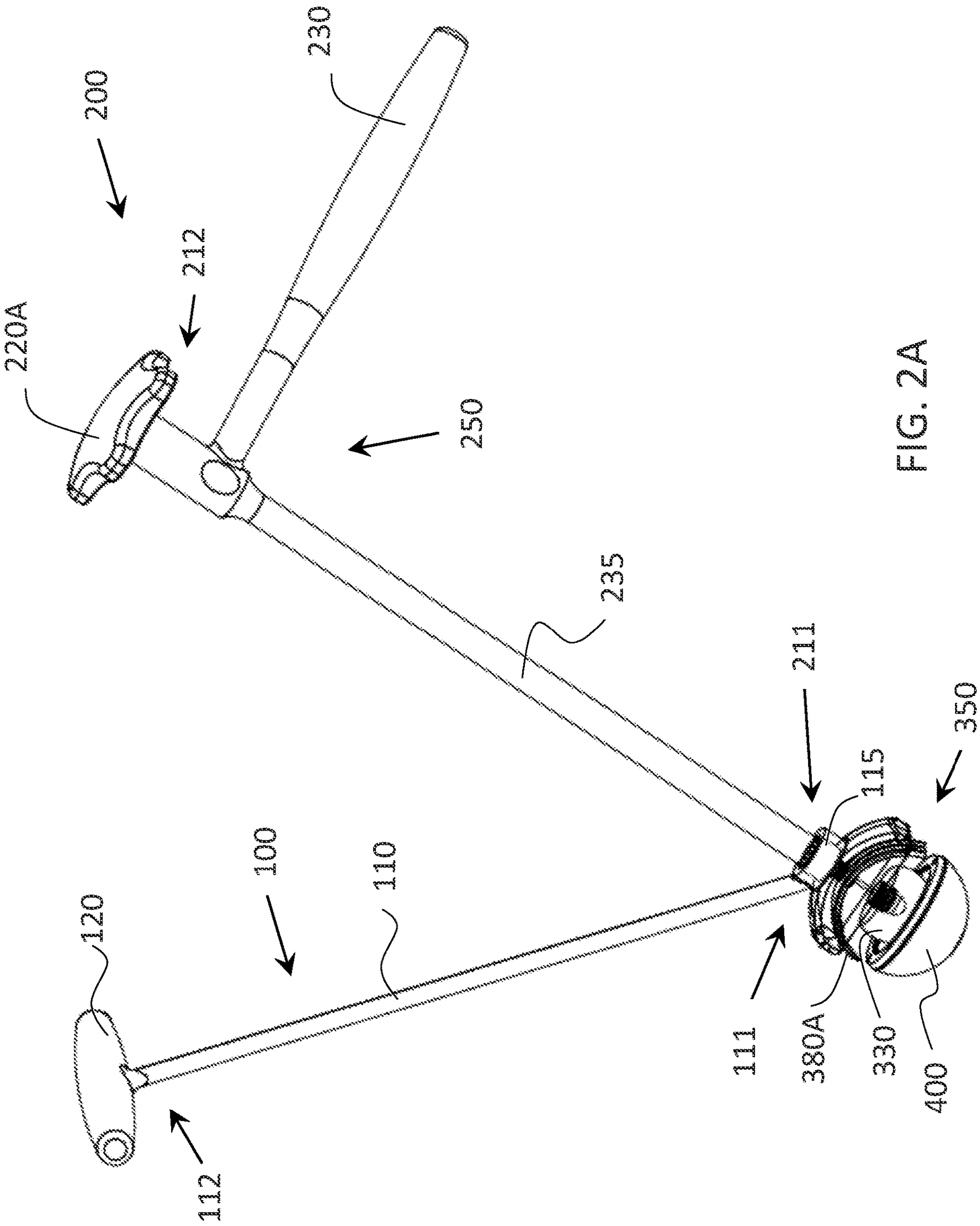
FIG. 2A is a front-side perspective view of one exemplary embodiment of an acetabular cup remover assembly in the assembled configuration featuring an extendable cutting blade.
Figure 2B:
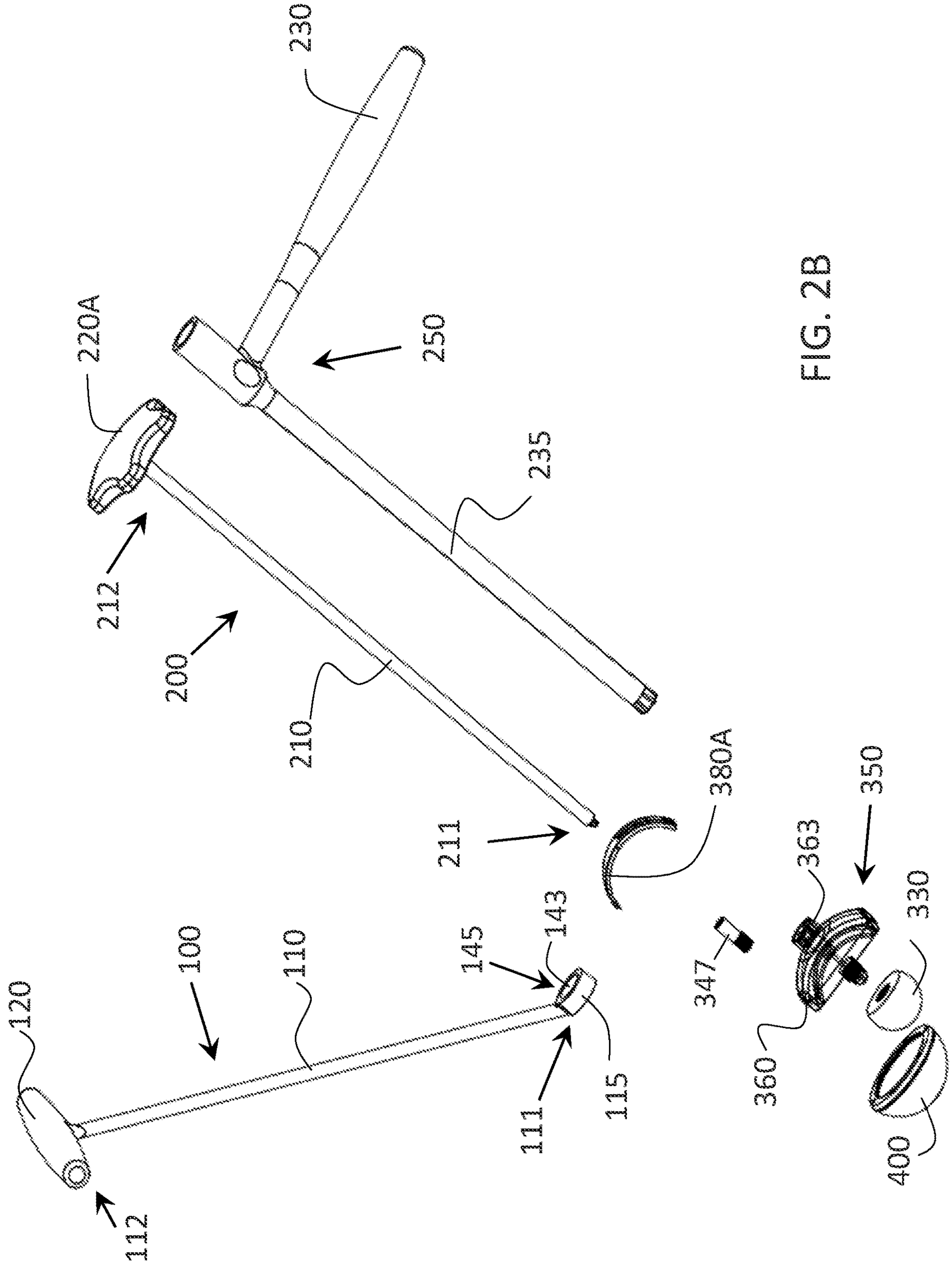
FIG. 2B is an exploded perspective view of the exemplary acetabular cup remover assembly of FIG. 2A in the disassembled configuration.
Figure 2C:
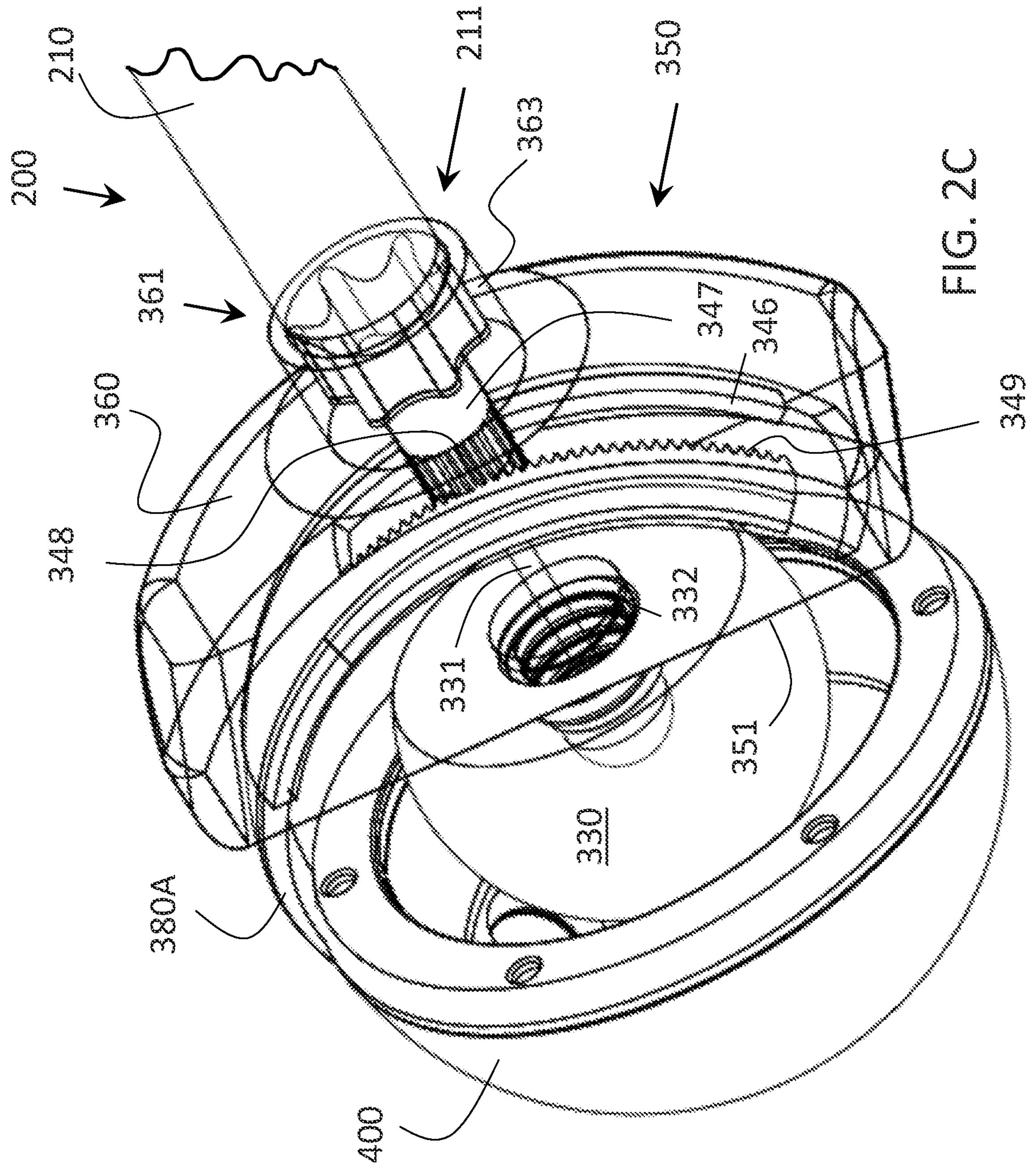
FIG. 2C is a detailed perspective view of the exemplary cutting assembly and exemplary cutting assembly support of FIGS. 2A and 2B and the acetabular shell implant.

The exemplary cup remover instrument assemblies 1 include, generally, a positioning member 100 comprising a longitudinal body 110, a leading end 111, and a trailing end 112. The longitudinal body 110 extends between the leading end 111 and the trailing end 112. The positioning member engages an orientation bearing 115 having an inner surface 143 (FIG. 2B) defining a through hole 145 (FIG. 2B). A cutting assembly 350 having a mating portion 363 (FIG. 2B) is configured to be rotatably disposed within the through hole 145 of the orientation bearing 115. Referring briefly to FIG. 2C, the mating portion 363 can comprise an outer circumferential surface. Referring briefly to FIGS. 2A and 2B, the inner surface 143 of the orientation is concentrically and closely disposed around the outer circumferential surface of the mating portion 363 when the cup remove instrument 1 is in the assembled configuration. In this manner, the mating portion 363 can be said to be "configured to be rotatably disposed within the through hole 145 of the orientation bearing 115."

The cutting assembly 350 comprises a cutting blade 380. A drive member 200 having a drive member body 210 (FIG. 2B) extends between a drive member leading end 211 and a drive member trailing end 212. The leading end 211 of the drive member 200 engages the cutting assembly 350 to rotatably drive the cutting assembly 350 to cut around the acetabular cup implant 400 and thus detach the acetabular cup implant 400 from a patient's natural acetabulum. It is contemplated that the positioning member 100, drive member 200 orientation bearing 115, and cutting assembly 350 can be made from medical grade stainless steel, titanium, or any other biocompatible material having similar strength and durability properties.

Various configurations of cutting arrangements and drive mechanisms for operating the various cutting arrangements will be described herein. In certain exemplary embodiments, the positioning member 100 is sized and configured to operate in or through a main incision, while the drive member 200 is sized and configured to operate in or through a portal incision.

Fixed Blade

In the embodiment of FIG. 1, the exemplary cup remover assembly 1 includes a single fixed cutting blade 380 that can be rotated around the outer edge of an acetabular cup implant 400 (see FIG. 2A). The positioning member 100 includes a longitudinal body 110, such as a main shaft or an extension portion extending between a leading or lower end 111 and a trailing or upper end 112. An orientation bearing 115 is affixed to or can be integral with the leading end 111. In exemplary embodiments, the orientation bearing 115 is a ring member configured to rotatably receive and support a cutting assembly 350. In embodiments, a hand grip 120 is provided on or adjacent to the trailing end 112 of the longitudinal body 110. The hand grip 120 can be in the form of a T-handle, as shown in FIG. 1. The hand grip 120 is configured for use in inserting the positioning member 100 and the cutting assembly 350 into a main incision that is aligned with the patient's hip joint. A partially engaged configuration, in which the positioning member 100 engages the cutting assembly 350 can be used to position the cutting assembly 350 over the patient's acetabulum and to seat a femoral head bearing 330 into the acetabular cup implant 400 that is to be removed.

A cutting assembly 350 is rotatably attached adjacent to the leading end 111 of the positioning member 100 via the orientation bearing 115. In the depicted embodiment, the cutting assembly 350 comprises a cutting assembly support 360 rotatably connected to the orientation bearing 115 in an assembled or partially assembled configuration, a cutting blade 380 extending distally from the cutting assembly support 360, and a femoral head bearing 330. The femoral head bearing 330 is positioned below the cutting assembly support 360. The femoral head bearing 330 is typically generally hemispherical and is typically sized for use in orienting the cup remover assembly 1 in the primary acetabular cup 400 (see FIG. 2A). The femoral head bearing 330 may be rotatably connected below the cutting assembly support 360 such that the cutting assembly support 360 rotates around and independently of the femoral head bearing 330. As shown in FIG. 1, the cutting blade 380 typically extends distally from the cutting assembly support 360 and has a curved or arcuate cross section generally matching an outer diameter of the acetabular cup implant 400 to be removed. The cutting blade 380 is positioned a selected distance from an outer diameter of the femoral head bearing 330 such that the cutting blade 380 cuts bone or bone cement adjacent an outer diameter of the acetabular cup implant 400 to be removed. A driver seat 361 (FIG. 2C) extension of the cutting assembly support 360 can be rotatably positioned in the orientation bearing 115 for use in rotating the cutting assembly support 360 and the cutting blade 380, as described herein.

Figure 4A:
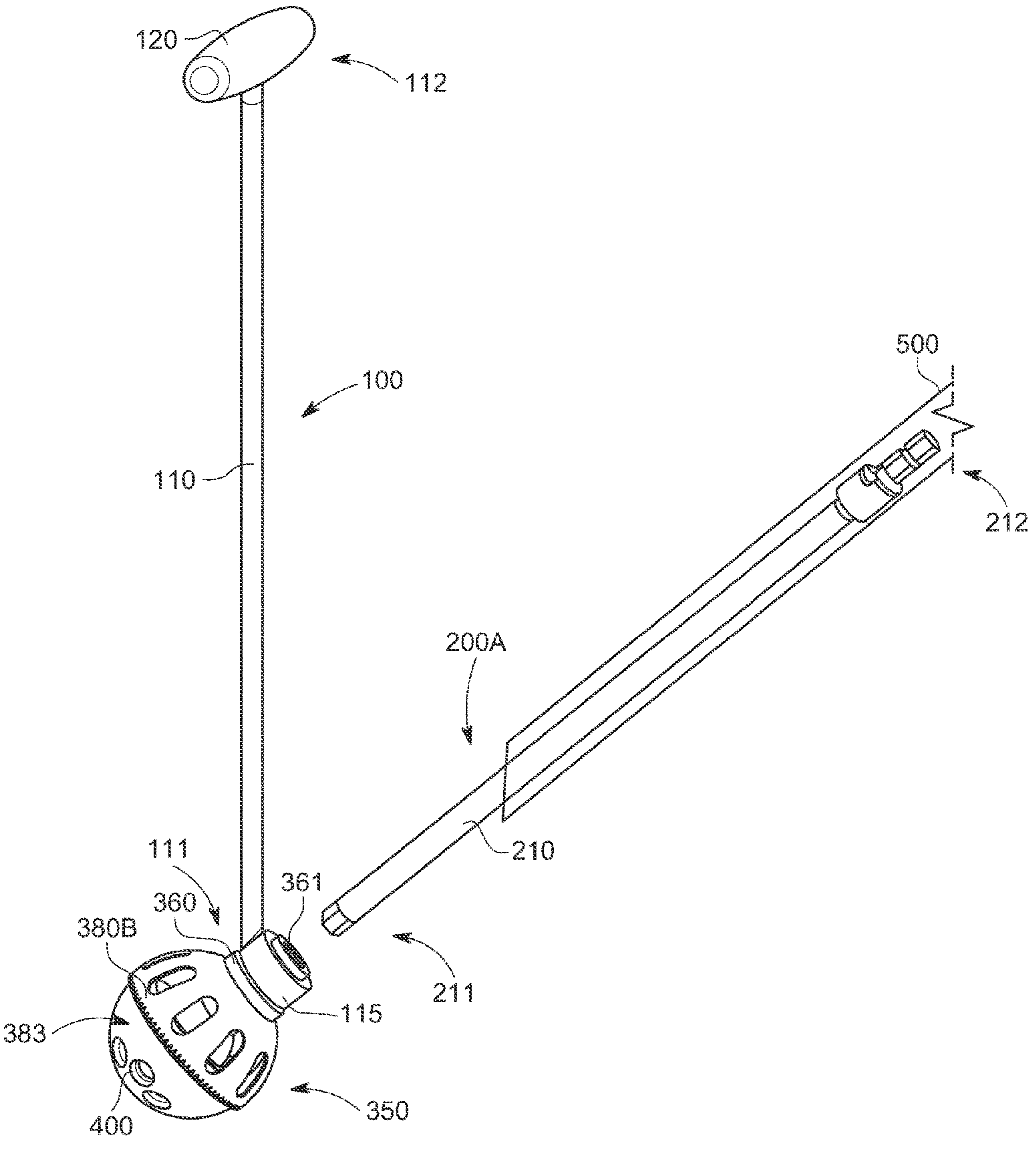
FIG. 4A is a side perspective view of an exemplary embodiment of a cup remover assembly in a partially assembled configuration featuring a hemispherical cutting blade.

A separate drive member 200 is provided for use in rotating the cutting assembly 350. The drive member 200 (see also FIG. 2B) has a drive member body 210 extending between a drive member leading or lower end 211 and a drive member trailing or upper end 212. In the embodiment of FIG. 1, the drive member body 210 has been inserted through a portal guide assembly 250. The portal guide assembly 250 can comprise a portal guide 235 that can be inserted through a portal incision in the patient's leg if desired. In other exemplary embodiments, the portal guide assembly 250 can be inserted through a cannula 500 (FIG. 4A). The portal guide assembly 250 may optionally include a drive handle 230 extending from the portal guide 235 adjacent to the drive member trailing end 212 in the assembled configuration. The drive handle 230 is desirably positioned and configured for use in rotating the drive member 200 to rotate the cutting assembly support 360 and the attached cutting blade 380 via the drive seat 161 when engaged. The drive handle 230 engages the drive member trailing end 212 in any manner appreciable by those having ordinary skill in the art, but desirably by a mechanical projection-receiver engagement mechanism as discussed below with reference to the leading end 211 of the drive member 200. In this manner, the drive handle 230 can be said to be "configured to" engage the drive member trailing end 212 to thereby rotate the drive member body 210 and the drive member leading end 211.

The leading end 211 of the drive member 200 is configured to engage the drive seat 361 of the cutting assembly support 360, such as via a male hex on the leading end 211 and a female hex on the drive seat 361, or vice versa. All projections and closely fitting receiver engagement mechanisms known to those having ordinary skill in the art are considered to be within the scope of this disclosure. In this manner, the drive member leading end 211 can be said to be "configured to engage the cutting assembly 350 to rotatably drive the cutting assembly 350." A handle 220 is provided on or at the trailing end 212 of the drive member 200 for use in holding, inserting, removing, and manipulating the drive member 200 in the portal guide assembly 250 and into engagement with the drive seat 361 disposed within the orientation bearing 115 of the positioning member 100.

Using the configuration described herein, a surgeon can selectively position the positioning member 100 in a main incision and the drive member 200 in a portal incision and selectively rotate the drive member 200 to rotate the cutting blade 380 around the acetabular cup implant 400 that is to be removed.

In order to accommodate and remove diverse sizes of acetabular cup implants (i.e., hip cups), the fixed cutting blade 380 is configured to be removable such that different sized cutting blades 380 can be selected for use in removing different sizes of cups. In exemplary embodiments, multiple sizes of cutting assembly supports 360, cutting blades 380, and femoral head bearings 330 may be provided, such as in the form of an instrument kit arranged in a surgical tray.

For example, it is contemplated that the cutting assembly support 360 has a length dimension that can be sized along with the cutting blade 380 to place the cutting blade 380 just outside of the outer diameter of the acetabular cup implant 400 to be removed. The size of the acetabular cup implant 400 is desirably known prior to surgery (e.g., through patient records or pre-operative radiographs) such that the cutting assembly support 360 and the cutting blade 380 can be sized to accommodate the removal of the acetabular cup implant 400. However, it is also contemplated that more than one cutting assembly supports 360 or cutting blades 380 having different size dimensions can be provided at the time of surgery to provide the surgeon with options when the surgeon encounters the actual acetabular cup implant 400 during the procedure.

It is further contemplated that fixed cutting blades 380 having different blade lengths can be provided. A surgeon may use a shorter cutting blade 380 to initiate the removal of the acetabular cup implant 400. For example, a shorter cutter blade 380 may create a useful opening between the natural acetabulum and the acetabular cup implant 400 around the outer circumference of the acetabular cup implant 400. A longer cutting blade 380 placed within the initial opening can be used to extend the opening between the acetabular cup implant 400 and the natural acetabulum to thereby separate the acetabular cup implant 400 from the natural acetabulum.

Differently sized femoral head bearings 330 may be used to seat various sized acetabular cup implants 400. In exemplary embodiments, the various sizes are integral with a respective positioning member 100. In other embodiments, the components may be removable from and detachable from a positioning member 100 so as to reduce instrument inventory.

Extendable Blade

In the embodiment of FIGS. 2A-C, the cup remover assembly 1 is similar to the exemplary embodiment described with reference to FIG. 1. However, the cutting blade 380 is selectively extendable from the cutting assembly support 360 (see FIG. 2C). In the embodiment of FIGS. 2A-C, this is accomplished by providing a hollow portal guide 235 that houses the drive member body 210. An adjustment handle 220A is provided on the trailing end 212, rather than the fixed handle 220 of the embodiment of FIG. 1. The selectively extendable cutting blade 380A is operably connected to the drive member 200 (FIG. 2B) such that rotation of the adjustment handle 220A, e.g., as in a clockwise direction, selectively extends the cutting blade 380A. Once a desired cutting blade length has been set, the surgeon can disengage the drive member 200 from the cutting assembly 350 to define a partially engaged position (i.e., the orientation bearing 115 of the positioning member 100 is still disposed around the mating portion 363 of the cutting assembly 350). The surgeon may then use the handle 120 of the positioning member 100 to selectively move the cutting assembly, and by extension, the selectively extendable cutting blade 380A around the outer surface of the acetabular cup implant 400 to thereby unseat the acetabular cup implant 400 from the patient's natural acetabulum. The length of the selectively extendable cutting blade 380A can be adjusted as needed relative to the bottom 351 of the cutting assembly support 360 during the procedure.

FIG. 2C provides a close up view of an exemplary operable connection of the cutting blade 380 to the drive member 200. In the assembled configuration, the leading end 211 of the drive member 200 comprises a male keyed shape, such as a hex shape. The male keyed shape is disposed in and engages the sides of a complementary keyed shape, such as a female hex shape on the drive seat 361. In this manner, the drive seat member 361 can be said to have a proximal end that has a keyed interface that is "configured to mate" with a complementary keyed inface of the drive member leading end 211.

The drive seat 361 is disposed within the mating portion 363 of the cutting assembly 350. In an assembled configuration, the mating portion 363 is disposed within the hole 145 of the preferably annular inner surface 143 of the orientation bearing 115. In this manner, the mating portion 363 can be said to be "configured to be rotatably disposed" within the hole 145 of the orientation bearing 115. While an annular inner surface 143 comprises a preferred embodiment, any mechanical engagement that permits the mating portion 363 to be positioned relative to the movement of an engaged positioning member 100 is considered to be within the scope of this disclosure.

The drive seat 361 is engaged to and shares a rotational axis with a spline shaft 347 comprising distal spline teeth 348. The distal spline teeth 348 in turn selectively engage geared teeth 349 of the extendable cutting blade 380. The geared teeth 349 can be oppositely disposed from a non-geared blade support side 346. In this manner, rotation of the adjustment handle 220A, e.g., as in a clockwise direction, selectively extends the cutting blade 380A relative to the bottom 351 of the cutting assembly support 360. The foregoing description is one example of how a cutting assembly support 360 can have a drive seat that is "configured to communicate with" the cutting blade 380.

In certain exemplary embodiments, a sleeve may be closely disposed between the spline shaft 347 and an inner wall of the drive seat 361. Such a sleeve can provide a frictional force that prevents rotation of the spline shaft 347 when said frictional force is not overcome by the rotational movement of the engaged drive member 200. In this manner the sleeve can lock the spline shaft 347, and by extension, the selectively extendable cutting blade 380A at the desired location, which can correspond to the desired length of the selectively extendable cutting blade 380A relative to the bottom 351 of the cutting assembly support 360.

It will be appreciated that a tangential protrusion and receiver locking mechanism or similar mechanical or electromechanical locking structure that prevents rotational movement of the spline shaft 347 when the engaged drive member 200 is not spinning is within the scope of this disclosure. The spline shaft 347 may be generally cylindrically and annularly disposed around a fixed femoral head bearing support 331 in exemplary embodiments. The fixed femoral head bearing support 331 extends beyond the spline shaft 347 and desirably supports a femoral head engagement mechanism 332. The femoral head engagement mechanism is configured to detachably engage a femoral hear bearing 330. Exemplary femoral head engagement mechanisms 332 can comprise a screw thread, a ball bearing in a complementary socket, a clamp, a protrusion, a recess, and other known means to selectively engage and disengage one component from another mechanically.

Figure 3:
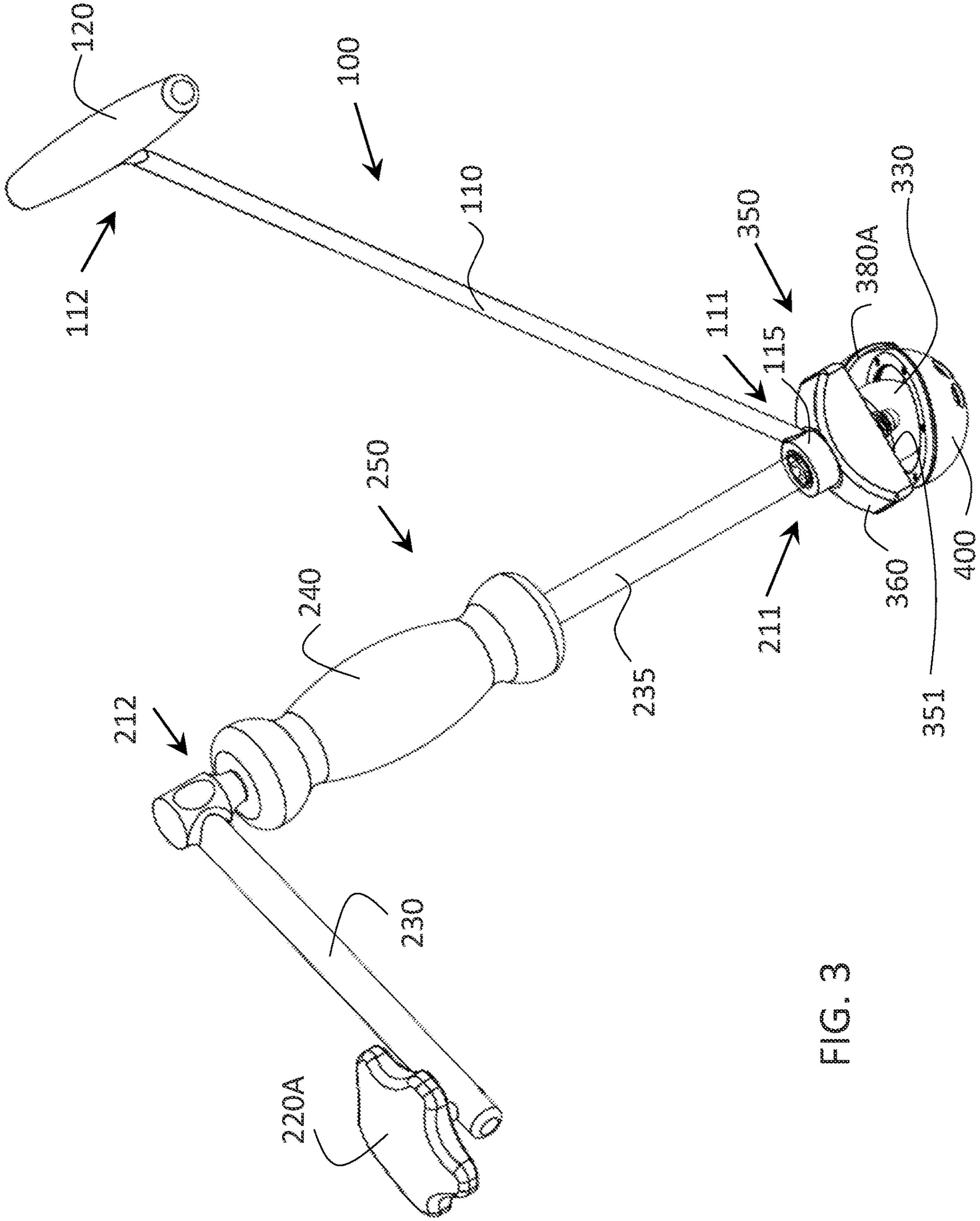
FIG. 3 is a front-side perspective view of an exemplary embodiment of an acetabular cup remover assembly in the assembled configuration featuring an extendable cutting blade, with the extension of the cutting blade timed to the rotation of a handle.

FIG. 3 shows an alternative embodiment of a selectively extendable cutting blade 380A in which the extension of the blade 380 is timed to the rotation of the drive handle 230. In this embodiment, the blade 380 extends a small amount relative to the bottom 351 of the cutting assembly support 360 with each rotation of the drive handle 230. In this manner, the cutting blade 380 cuts deeper with each rotation. In the embodiment of FIG. 3, this is accomplished by providing the drive member 200 (see FIG. 2B) through the portal guide 235 of the portal guide assembly 250. The portal guide assembly 250 may optionally further comprise a fixed handle 240 on the upper portion of the portal guide 235 for use in holding and manipulating the dive member 200. As with the embodiments depicted in FIG. 1 and FIGS. 2A-C, the portal guide assembly 250 can be inserted through a portal incision in the patient's leg if desired. In other exemplary embodiments, the portal guide assembly 250 can be inserted through a cannula 500 (FIG. 4A). The cutting blade 380 is operably connected to the internal drive member 200 such that rotation of the drive handle 230, e.g., as in a clockwise direction, selectively extends the cutting blade 380. In the depicted embodiment, the cutting blade 380 is operatively connected to the drive member 200 and can be selectively lockable in the same way as described with reference to FIG. 2C above.

Powered Blade

In the embodiment of FIG. 4A, the detachable cup remover assembly 1 of the present disclosure includes a powered hemispherical cutting blade 380B. In the embodiment of FIG. 4A, the hemispherical cutting blade 380B has a hollow hemispherical interior and an annular rim on a lower end thereof. The hemispherical cutting blade 380B is provided with a cutting edge (see 383) along the annular bottom rim, such as a serrated edge or serrations in the manner of a saw blade. The hemispherical cutting blade 380B desirably comprises one or more evacuation holes 385 extending through a blade body of the hemispherical cutting blade 380B. The evacuation holes 385 permit removed bone cement, bone, marrow, or other tissue to exit the drilling area without unduly interfering with the cutting process.

In embodiments, various sizes of hemispherical blades 380B are provided such that the blade 380B can be selectively matched to the size of a primary or revision acetabular cup implant 400 to be removed. The annular rim is selectively sized to extend a cutting end of the hemispherical cutting blade 380B around the fixed primary or revision acetabular cup implant 400. The hemispherical cutting blade 380B can be power driven by the drive member 200, which in this embodiment takes the form of a portal drive shaft 200A. A trailing end 212 of the portal drive shaft 200A is provided with a standard configuration for engagement by an electric drill or other power drive mechanism, such as an engagement flat or flats.

Figure 4C:
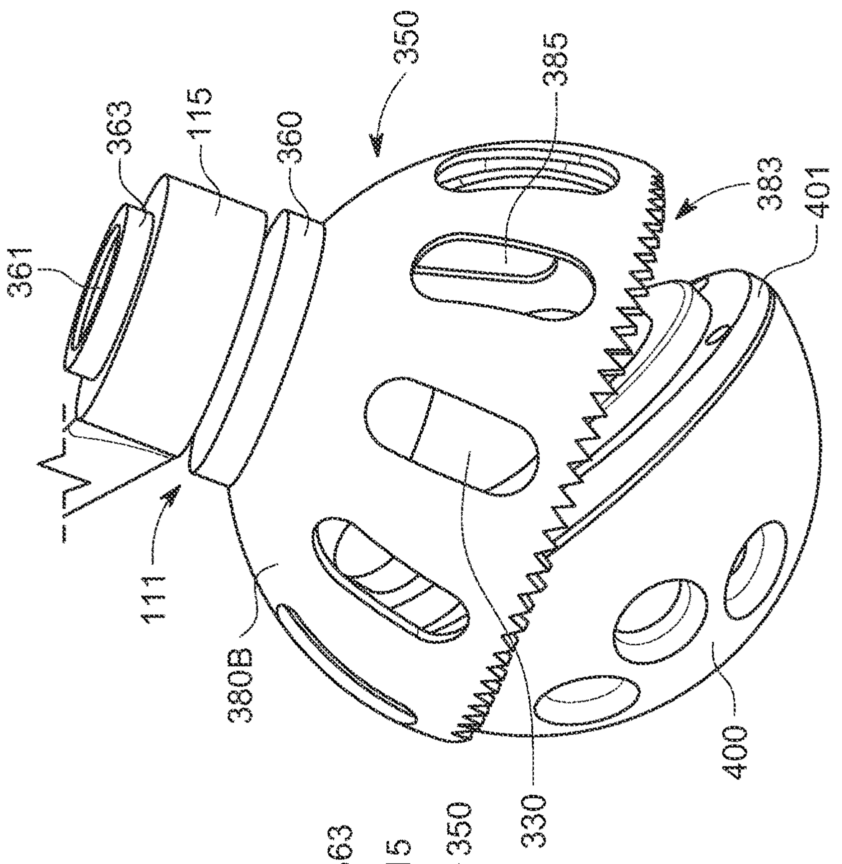
FIG. 4C is a perspective side view of the hemispherical cutting blade of FIG. 4A showing the hemispherical cutting blade aligned to cut around the side of the acetabular shell implant.
Figure 4B:
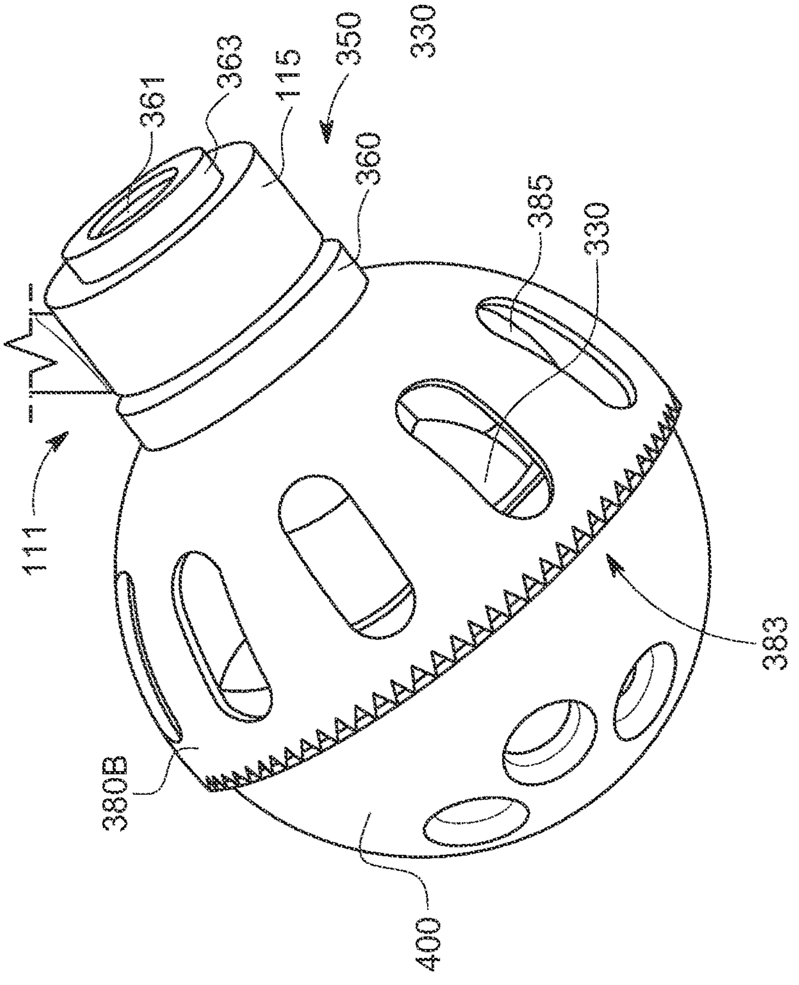
FIG. 4B is a side perspective view of the hemispherical cutting blade of FIG. 4A showing the hemispherical cutting blade aligned over the top of an acetabular shell implant (i.e., a hip cup).

As indicated in FIGS. 4B and 4C (see also FIG. 4A), the T-handle 120 of the positioning member 100 can be used to move the hemispherical blade 380B around the outer diameter of the primary or revision acetabular cup implant 400 during cutting. FIG. 4B shows the hemispherical cutting blade 380B oriented directly over the acetabular cup implant 400 in a starting position. FIG. 4C shows the hemispherical cutting blade 380B rotated around a side of the acetabular cup implant 400 to assist in cutting deeper areas of the adjacent bone or bone cement.

The powered hemispherical cutting blade 380B, while powerful, presents several design limitations. Depending on the size of the inner diameter of the acetabular cup implant 400, a liner insert 401 may be needed in order to maintain the hemispherical cutting blade 380B in a concentric orientation with the outer diameter of the primary or revision acetabular cup implant 400. Liner inserts 401 can be provided to accommodate various sizes of acetabular cup implants 400 and hemispherical cutting blades 380B. Additionally, it is contemplated that the use of a portal drive shaft 200A having a ball end, universal joint (see 209, FIG. 5) or a gimbled connection (not shown) will improve maneuverability of any of the blades 380 considered to be within the scope of this disclosure around the acetabular cup insert 400 during cutting.

Figure 4D:
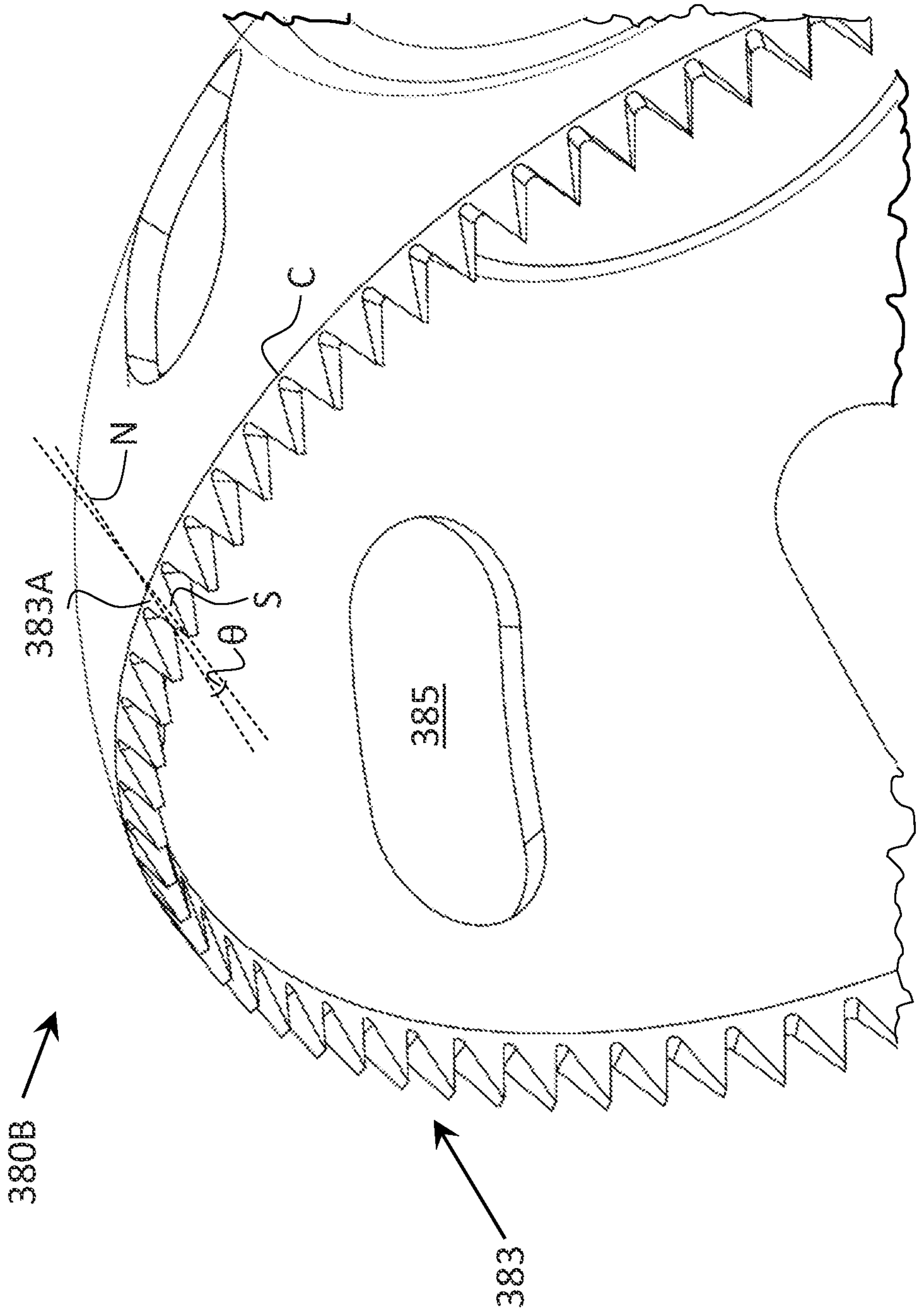
FIG. 4D is a close up perspective view of the hemispherical cutting blade of FIG. 4A, which further details serrated teeth extending from a circumference of the hemispherical cutting blade.
Figure 4E:
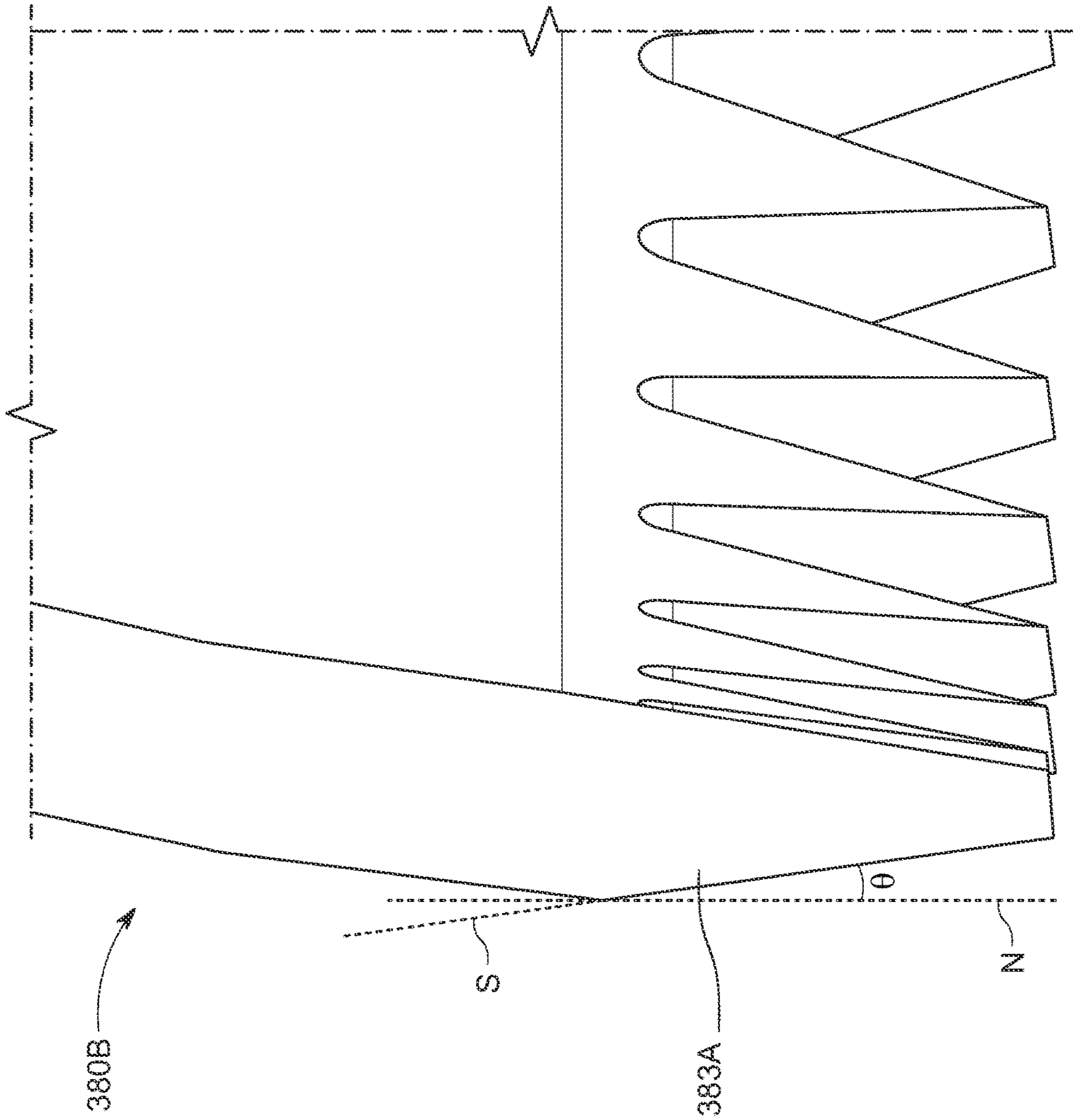
FIG. 4E is a close up side cross sectional view of the hemispherical cutting blade of FIG. 4A further detailing a cross section of a serrated tooth to further illustrate the outer surface angle.

As seen more clearly in FIGS. 4D and 4E, the serrated edge comprises serrated teeth 383 extending from a circumference C of the hemispherical cutting blade 380B. In the depicted embodiment, the serrated teeth 383 have an outer surface angle θ defined by the intersection between a normal line N to the circumference C of the hemispherical cutting blade 380B and the plane defined by an outer surface S of a serrated tooth 383A of the serrated teeth 383. In certain exemplary embodiments, the outer surface angle θ is desirably less than 10 degrees. In other exemplary embodiments, the outer surface angle θ can be a compound angle comprising the sum of multiple angles, including for example, combinations of outer surface angles and normal angles. In still other exemplary embodiments, the outer surface S of the serrated tooth 383A can comprise multiple outer surface angles θ wherein the second and any subsequent angles disposed below an initial angle, the initial angle being disposed closest to the circumference C, are greater than the preceding outer surface angle θ relative to the normal line N. In still other exemplary embodiments, the serrated teeth 383 may have a portion that is coextensive with the normal line N and be angled relative to a line that is coplanar with the normal plane to define a normal angle. In still other exemplary embodiments, outer surface S of the serrated tooth 383A can comprise multiple normal angles wherein the second and any subsequent angles are greater than the preceding normal angle relative to the line that is coplanar with the normal plane. Combinations of normal angles and outer surface angles θ are considered to be within the scope of this disclosure. Any arrangement of teeth 383 that closely follows the outer curvature of the acetabular cup implant 400 in in such manner that pulls the acetabular cup implant 400 toward the cutting assembly support 360 during operation is considered to be within the scope of this disclosure.

Without being bound by theory, it is contemplated that a hemispherical cutting blade 380B having serrated teeth 383 with an outer surface angle θ of desirably less than 10 degrees applies a pulling force on the acetabular cup implant 400 during active use. That is, the hemispherical cutting blade 380B with the serrated teeth 383 described herein may facilitate the removal of the acetabular cup implant 400 by drawing the acetabular cup implant 400 toward the bottom 351 of the cutting assembly support 360 during normal use. As a result, it is contemplated that surgeons may be able to spend less time removing prior-implanted acetabular cup implants 400, to thereby reduce procedure time and its ancillary risks.

The components of the cup remover instrument assembly 1, including different sizes of components, will typically be arranged in a convenient format, such as in a surgical tray or case, in the manner of a kit. However, the kit components do not have to be packaged or delivered together, provided that they are assembled or collected together in the operating room for use at the time of surgery.

Figure 5:
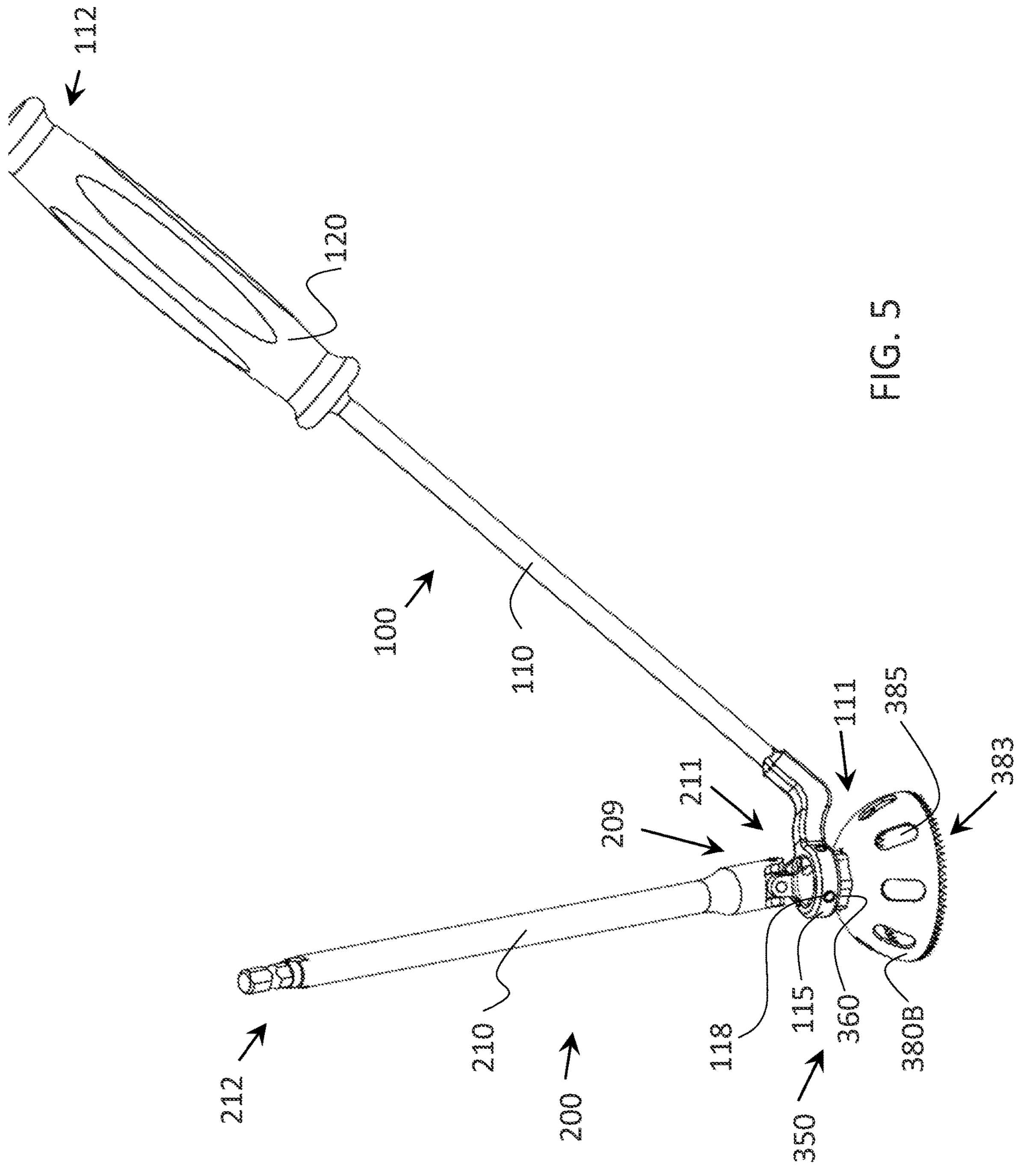
FIG. 5 is a perspective side view of another exemplary embodiment of a cup remover assembly in the assembled configuration featuring a hemispherical cutting blade, an orientation bearing integrally engaged to the leading end of a positioning member, and a cutting assembly support rotatably engaged to the drive member via a universal joint.

FIG. 5 is a side perspective view of another exemplary embodiment of the present disclosure in which the orientation bearing 115 is directly integrally engaged to the leading end 111 of the positioning member 100 and wherein the annular inner surface 143 of the orientation bearing 115 further comprises ball bearings 118 disposed within the orientation bearing 115 and extending into the hole 145 of the orientation bearing 115. In an assembled configuration, or in a partially assembled configuration in which the cutting assembly 350 is rotatably disposed within the hole 145 of the orientation bearing 115, the ball bearings 118 can be closely disposed adjacent to a track in the cutting assembly support 360 to facilitate the rotational movement of the cutting assembly support 360 relative to the orientation bearing 115.

In the depicted embodiment, the drive member 200 comprises a universal joint 209 at the drive member leading end 211. In practice, it is contemplated that the drive member 200, which is a portal drive shaft as in the depicted embodiment, may be inserted through a portal incision in the patient's leg that aligns with the exposed surgical area. The exposed surgical area can be defined by a main surgical incision positioned over the patient's joint capsule relative to the surgeon's point of view. The surgeon may place the cutting assembly 350 comprising a cutting assembly support 360 and a hemispherical cutting blade 380 into the main incision. The cutting assembly 350 may be rotatably engaged to the orientation bearing 115, which is in turn directly or indirectly engaged to the positioning member 100 while inserted into the main incision. The drive member 200 may be inserted into the portal incision. A cannula 500 or other tube may be inserted through the portal incision prior to the insertion of the drive member 200. A cannula 500 or other liner can be desirable to preserve patient tissue surrounding the portal incision in view of the rotational movement of the drive member 200. Once both the cutting assembly 350 and the drive member leading end 211 are present in the main surgical area, the surgeon then engages the drive member leading end 211 to the drive seat 361 of the cutting assembly 350. In the depicted embodiment, the drive seat 361 of the cutting assembly 350 is disposed on a trailing end (see 111) of a universal joint 209 (see FIG. 6). The depicted universal joint 209 can be part of the cutting assembly support 360. The cutting assembly support 360 in turn supports the cutting blade 380, which is a hemispherical cutting blade 380B in the depicted embodiment.

Without being bound by theory, it is contemplated that the presence of the universal joint 209, or a similar omnidirectional joint, permits the surgeon to use the positioning member 100 to adjust the position of the hemispherical cutting blade 380B in an arcuate manner relative to the acetabular cup implant 400 (see FIGS. 4B and 4C) while maintaining the rotational movement of the hemispherical cutting blade 280B around a center rotational axis R via the drive member 200. Such an embodiment may permit surgeons to use a portal incision and main incision minimally invasive technique to remove the prior-installed acetabular cup implant 400 in a revision hip arthroplasty procedure. It is contemplated that the speed at which this may be accomplished could reduce the overall time that the patient is under anesthesia, reduce procedure time, and therefore the risk of infection, while maintaining the enhanced recovery time associated with minimally invasive procedures.

Although a universal joint 209 is depicted, all joints that permit variations in alignment or distance between the drive member 200 and the cutting assembly support 360 are considered to be within the scope of this disclosure, including for example: jaw couplings, rag joints, splined joints, a balled end and gimbled connection, and prismatic joints.

Figure 6:
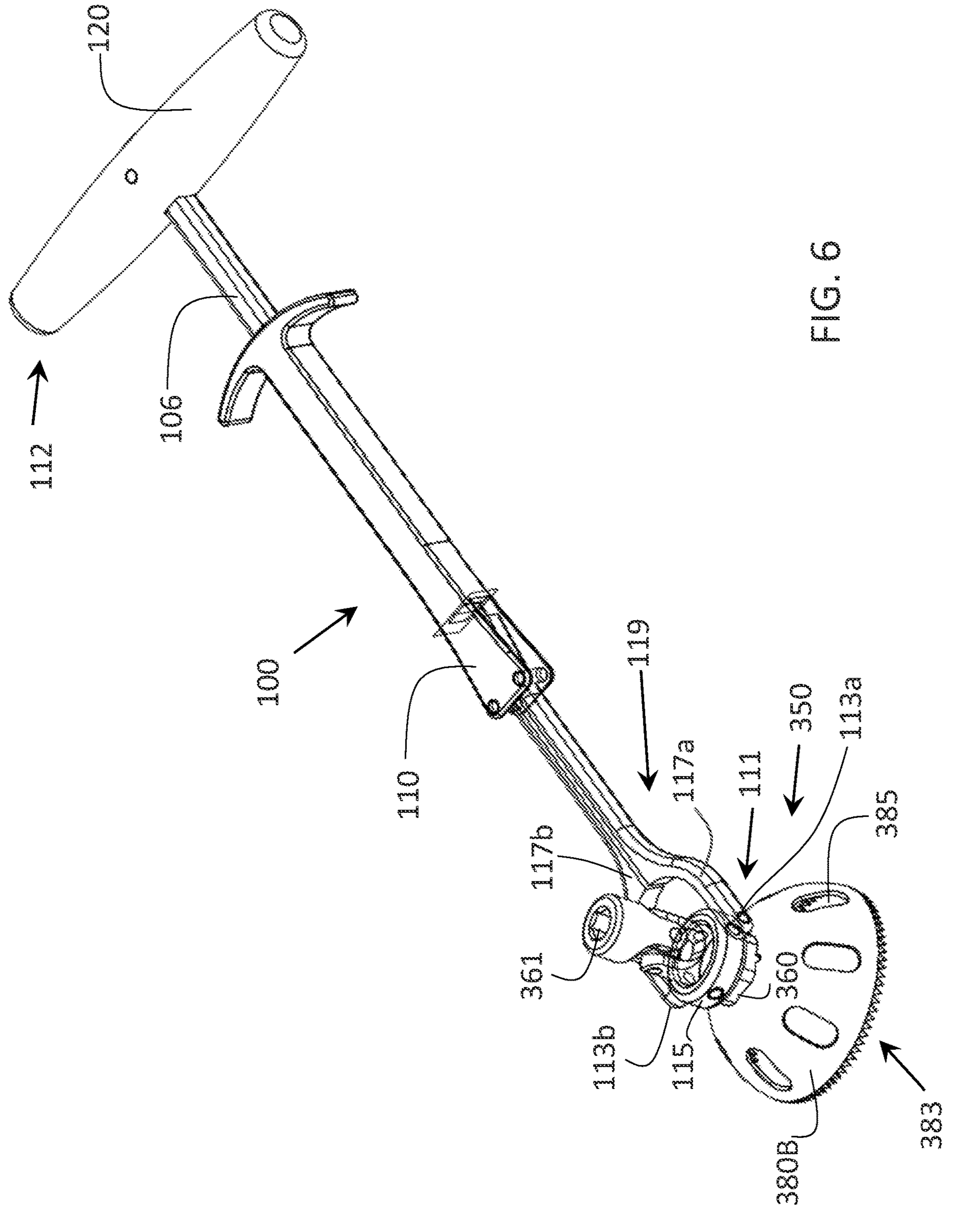
FIG. 6 is a side perspective view of an exemplary embodiment of a cup remover assembly in the assembled configuration in which the positioning member further comprises an articulating clamp comprising a first arm and a second arm configured to indirectly engage the orientation bearing.

FIG. 6 is a side perspective view of an exemplary cup remover instrument assembly 1 that is similar to the embodiment described with reference to FIG. 5, except that the positioning member 100 further comprises an articulating clamp 119 at the leading end 111. The articulating clamp 119 comprises a first arm 117*a* and a second arm 117*b* oppositely and distally disposed to the first arm 117*a*. Pins 113*a*, 113*b* extend through aligned pin holes in the orientation bearing 115 and in the first arm 117*a* and the second arm 117*b* to indirectly engage the orientation bearing 115 to the leading end 111 of the positioning member 100. In this manner, the positioning member 100 can be said to "indirectly engage" the orientation bearing 115. In the depicted embodiment, the T handle 120 of the positioning member 100 engages a trailing end of a follower 106. The surgeon can apply a counter force when pressing the T handle 120 and the follower 106 toward the leading end 111 of the positioning member 100. The follower 106 extends generally within the positioning member 100 along the length of the positioning member 100 until the follower 106 reaches the articulating clamp 119. A surgeon can push the follower 106 toward the leading end 111 to extend the first arm 117*a* and the second arm 117*b* away from one another to release the orientation bearing 115.

Figure 7:
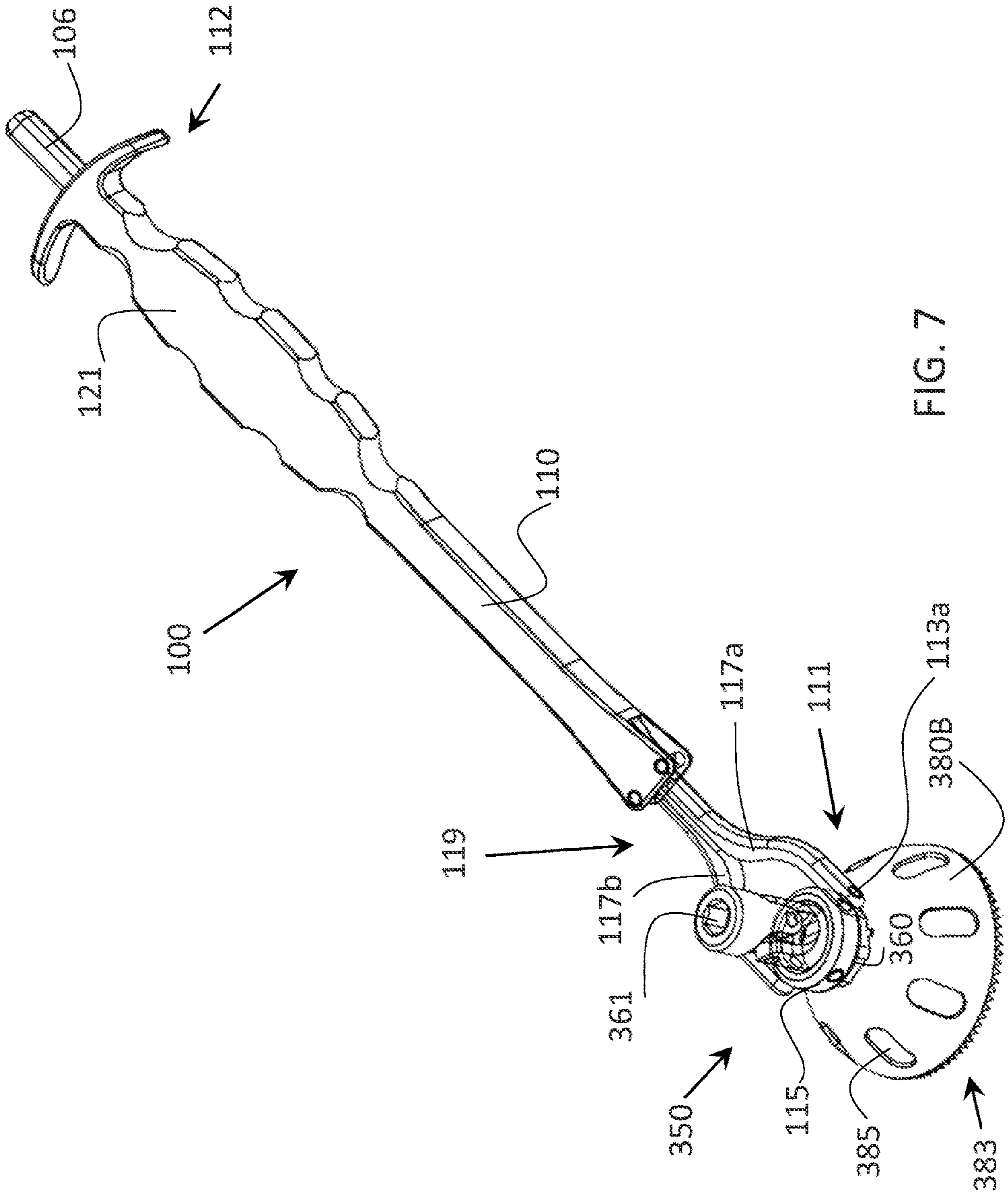
FIG. 7 is a side perspective view of an exemplary embodiment of a cup remover assembly in the assembled configuration similar to the embodiment of FIG. 6 but having a more ergonomic handle.

The exemplary embodiment of FIG. 7 is similar to the exemplary embodiment of FIG. 6 except that the body 110 of the positioning member 100 comprises a grip 121 that extends generally lengthwise along the length of the body 110 of the positioning member 100. The follower 106 may engage a T handle 120 as shown in FIG. 6, a different type of handle, or no handle at all.

The instruments that comprise the exemplary cup remover instrument assembly 1 can be provided in the form of a kit. The components of the kit are preferably arranged in a convenient format, such as in a surgical tray or case. However, the kit components do not have to be packaged or delivered together, provided that they are assembled or collected together in the operating room for use at the time of surgery. An exemplary kit can include any suitable embodiment of a cup remove instrument assembly 1, variations of the cup remove instrument assembly 1 described herein, and any other cup remove instrument assembly 1 according to an embodiment. While it is contemplated that an exemplary kit may further include one or more cutting assemblies 350, one or cutting blades 380, one or more types of cutting blades 380, (e.g., selectively extendable cutting blades 380A, or hemispherical cutting blades 380B), one or more drive members 200, one or more cutting assembly supports 360, one or more orientation bearings 115, and one or more positioning members 100, it will be appreciated that certain kits may lack some or all of these elements. Any suitable embodiment of a cutting assembly 350, variations of the cutting assemblies 350 described herein, and any other cutting assemblies 350 according to an embodiment are considered to be within the scope of this disclosure. Any suitable embodiment of a cutting blade 380, variations of the cutting blades 380 described herein, and any other cutting blade 380 according to an embodiment are considered to be within the scope of this disclosure. Any suitable embodiment of a drive member 200, variations of the drive members 200 described herein, and any other drive member 200 according to an embodiment are considered to be within the scope of this disclosure. Any suitable embodiment of a cutting assembly support 360, variations of the cutting assembly supports 360 described herein, and any other cutting assembly support 360 according to an embodiment are considered to be within the scope of this disclosure. Any suitable embodiment of an orientation bearing 115, variations of the orientation bearings 115 described herein, and any other orientation bearing 115 according to an embodiment are considered to be within the scope of this disclosure. Any suitable embodiment of a positioning member 100, variations of the positioning members 100 described herein, and any other positioning member 100 according to an embodiment are considered to be within the scope of this disclosure.

Selection of a suitable number or type of cup remover instrument assembly 1, cutting assembly 350, cutting blade 380, drive member 200, cutting assembly support 360, orientation bearing 115, and positioning member 100 to include in a kit according to a particular embodiment can be based on various considerations, such as the procedure intended to be performed using the components included in the kit.

Methods of Use

In operation, the cup remover 1 is configured for use in a two-incision hip procedure, such as those discussed in the background section, which are incorporated herein by reference in their entireties. In two-incision hip procedures, a main incision provides access to the hip joint, while a nearby portal incision communicates with the hip joint. Relatively large instruments are inserted into the hip joint through the main incision, while the portal incision is used to drive or otherwise operate the instruments located in the hip joint. Two-incision hip procedures have traditionally been used for primary hip procedures. However, the cup remover 1 of the invention is designed for use in two-incision revision procedures. As discussed above, the positioning member 100 is sized and configured to operate in or through a main incision, while the drive member 200 is sized and configured to operate in or through a portal incision. The positioning member can be manipulated in the main incision via the hand grip 120 and the upper portion of the extension portion 120. The configuration of the drive member 200 allows it to be inserted through a portal incision and operated via the handle 220 and drive handle 230 portions. If a cannula 500 is used in the portal incision, a portal drive shaft 200 can be inserted into the cannula 500 and used to drive the cutting blade 380.

An exemplary medical device assembly comprises: an orientation bearing having an inner surface defining a hole, a positioning member engaged to the orientation bearing, the positioning member having a longitudinal body extending between a leading end and a trailing end, a cutting assembly having a mating portion configured to be rotatably disposed within the hole of the orientation bearing, wherein the cutting assembly comprises a cutting blade, and a drive member having a drive member body extending between a drive member leading end and a drive member trailing end, wherein the drive member leading end is configured to engage the cutting assembly to rotatably drive the cutting assembly.

In an exemplary embodiment, the medical device assembly can further comprise a femoral head bearing disposed below a blade support portion.

In an exemplary embodiment, the cutting assembly can further comprise: a blade support portion rotatably connected to the cutting assembly support. In yet a further exemplary embodiment, the blade support portion is a drive seat configured to communicate with the cutting blade, and the cutting blade extends distally from the blade support portion, and the leading end of the drive member is configured to engage the drive seat.

In an exemplary embodiment, the orientation bearing is integrally engaged to the leading end of the positioning member. In another exemplary embodiment, the orientation bearing is indirectly engaged to the leading end of the positioning member.

In an exemplary embodiment, the cutting blade is a hemispherical cutting blade. In such an embodiment, the hemispherical cutting blade may further comprise serrated teeth extending from a distal circumference of the hemispherical cutting blade. In such an embodiment, the serrated teeth may further have an outer surface angle defined by an angle between a normal line to the distal circumference of the hemispherical cutting blade and an outer surface of a serrated tooth of the serrated teeth. In such an embodiment, the outer surface angle may be less than 10 degrees.

In an exemplary embodiment comprising a hemispherical cutting blade, the hemispherical cutting blade further defines an evacuation hole extending through a blade body of the hemispherical cutting blade. In such an exemplary embodiment, the hemispherical cutting blade may further define a plurality of evacuation holes extending through a blade body of the hemispherical cutting blade.

In an exemplary embodiment, the cutting assembly further comprises a cutting assembly support, and wherein the cutting assembly support has the mating portion configured to be rotatably disposed within the hole of the orientation bearing. In such an exemplary embodiment comprising a cutting assembly support, the medical device assembly may further comprise a drive seat member disposed between the cutting assembly support and the drive member in an assembled configuration. In such an exemplary embodiment comprising a cutting assembly support, the cutting assembly support may have a drive seat member configured to communicate with the cutting blade, the cutting blade can extend distally from the cutting assembly support, and the leading end of the drive member can be configured to engage the drive seat.

In an exemplary embodiment comprising a drive seat member, the drive seat member may comprise a proximal end having a keyed interface configured to mate with a complementary keyed interface of the drive member leading end.

In an exemplary embodiment having a keyed interface, the cutting blade is a curved cutting blade, wherein a spline shaft extends distally from the keyed interface, and wherein geared teeth on a distal end of the spline shaft engage complementary geared teeth of the curved cutting blade disposed in the cutting assembly support such that a rotational movement of the spline shaft translates into an arcuate movement of the curved cutting blade.

In an exemplary embodiment, the positioning member may further comprise an articulating clamp at the leading end, the articulating clamp may comprise a first arm and a second arm, and pins may extend through aligned pin holes in the orientation bearing and the first arm and the second arm to indirectly engage the orientation bearing to the positioning member.

In an exemplary embodiment, the medical device assembly may further comprise a handle disposed at the trailing end of the positioning member.

In an exemplary embodiment, the medical device assembly may further comprise a drive handle configured to engage the drive member trailing end to thereby rotate the drive member body and the drive member leading end.

In an exemplary embodiment, the cutting assembly is rotatably engaged to the cutting assembly support.

In an exemplary embodiment, the medical device assembly can further comprise a cannula, wherein the drive member is disposed within the cannula.

An exemplary medical device assembly can comprise: a cutting assembly support having a drive seat configured to communicate with a curved cutting blade, the curved cutting blade extending distally from the cutting assembly support, and a drive member having a drive member body extending between a drive member leading end and a drive member trailing end, wherein the drive member is configured to engage the drive seat to arcuately extend the curved cutting blade.

An exemplary medical device assembly can comprise: an orientation bearing having an inner surface defining a hole; a positioning member engaged to the orientation bearing, the positioning member having a longitudinal body extending between a leading end and a trailing end, a cutting assembly support having a mating portion configured to be rotatably disposed within the hole of the orientation bearing, a cutting assembly engaged to the cutting assembly support, wherein the cutting assembly comprises a cutting blade, and, a drive member having a drive member body extending between a drive member leading end and a drive member trailing end, wherein the drive member trailing end is configured to engage the cutting assembly support to rotatably drive the cutting assembly.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A medical device assembly comprising:

an orientation bearing having an inner surface defining a hole and an outer surface;

a positioning member engaged to the orientation bearing, the positioning member having a first longitudinal body extending between a leading end and a trailing end, the first longitudinal body defining a first longitudinal body axis, the leading end physically engaged to the outer surface of the orientation bearing;

a cutting assembly comprising an extendable blade, a blade support engaged to the extendable blade, a mating portion tube extending from the blade support and a spline shaft having spline teeth communicating with gear teeth of the extendable blade to extend the extendable blade when the spline shaft is rotated, the mating portion tube configured to be rotatably disposed within the hole of the orientation bearing, wherein the mating portion tube includes an exterior sidewall and an inner sidewall, and a drive seat is disposed within the mating portion tube, the drive seat having a first engagement surface; and a drive member having a drive member body and a portal guide assembly, wherein the portal guide assembly includes a hollow portal guide for housing the drive member body therein, the drive member body comprising a second longitudinal body extending between a drive member leading end and a drive member trailing end defining a second longitudinal body axis, the drive member body is configured to rotate around the second longitudinal body axis, the drive member leading end configured to engage the first engagement surface of the drive seat to rotate the spline shaft to extend the extendable blade, wherein the drive seat is engaged to and shares a rotational axis with the spline shaft, and physical contact between the drive member leading end and the first engagement surface of the drive seat is within the hole defined by the inner surface of the orientation bearing.

2. The medical device assembly of claim 1 further comprising a femoral head bearing disposed below the blade support.

3. The medical device assembly of claim 1 further comprising a handle disposed at the trailing end of the positioning member.

4. The medical device assembly of claim 1 further comprising a drive handle configured to engage the drive member trailing end to thereby rotate the drive member body and the drive member leading end.

5. The medical device assembly of claim 1 further comprising a cannula, wherein the drive member is disposed within the cannula.

6. The medical device assembly of claim 1, wherein the second longitudinal body axis of the drive member body is transverse to the first longitudinal body axis of the positioning member.

7. The medical device assembly of claim 1, wherein the first engagement surface is a first keyed surface having a female hex geometry, and the drive member leading end is a second keyed surface having a male hex geometry.

8. A medical device assembly comprising:

an orientation bearing having an inner surface defining a hole and an outer surface;

a positioning member physically engaged to the outer surface of the orientation bearing, the positioning member having a first longitudinal body extending between a leading end and a trailing end, the first longitudinal body defining a first longitudinal body axis;

a cutting assembly having a mating portion configured to be rotatably disposed within the hole of the orientation bearing, the cutting assembly further comprising an extendable cutting blade assembly and a spline shaft, wherein the extendable cutting blade assembly includes a first blade end with a cutting blade and a second blade end with first geared teeth, the spline shaft including a first shaft end positioned within the mating portion and a second shaft end with second spline teeth for engaging the first geared teeth of the extendable cutting blade assembly, wherein the mating portion includes an exterior sidewall and an inner sidewall, wherein a drive seat that includes a first keyed surface is disposed within the mating portion;

a drive member having a drive member body comprising a second longitudinal body extending between a drive member leading end and a drive member trailing end defining a second longitudinal body axis, the drive member body is configured to rotate around the second longitudinal body axis, the drive member leading end comprises a second keyed surface to engage the drive member to the first keyed surface of the drive seat, wherein the spline shaft extends distally from a keyed interface of the first keyed surface and the second keyed surface, and wherein the second spline teeth on the second shaft end of the spline shaft engage complementary said first geared teeth of the extendable cutting blade assembly such that a rotational movement of the drive member body to rotate the spline shaft translates into an arcuate movement of the cutting blade, wherein the second longitudinal body axis of the drive member body is transverse to the first longitudinal body axis of the positioning member such that the positioning member is configured to be inserted through a primary incision of a two-incision surgical procedure and such that the drive member is configured to be inserted through a separate portal incision of the two-incision surgical procedure.

9. The medical device assembly of claim 8, wherein the cutting blade is curved.

* * * * *